United States Patent [19]

Ishimura et al.

[11] Patent Number: 5,660,976
[45] Date of Patent: Aug. 26, 1997

[54] METHOD FOR PRESERVING A LIVER BY PERFUSION WITH OR STORAGE IN A SOLUTION CONTAINING ASCORBYL TOCOPHERYL PHOSPHODIESTER

[75] Inventors: Yuzuru Ishimura, Mitaka; Makoto Suematsu, Tokyo; Kenichi Yoshida, Ibaraki, all of Japan

[73] Assignee: Senju Pharmaceutical Co., Ltd., Osaka, Japan

[21] Appl. No.: 489,676

[22] Filed: Jun. 13, 1995

[30] Foreign Application Priority Data

Jun. 14, 1994 [JP] Japan ................... 6-131654

[51] Int. Cl.⁶ ............................. A01N 1/02; A61K 31/665
[52] U.S. Cl. ............................. 435/1.2; 514/100; 549/220
[58] Field of Search ..................... 435/2, 1.2; 514/100; 549/220

[56] References Cited

U.S. PATENT DOCUMENTS

| | | | |
|---|---|---|---|
| 4,948,786 | 8/1990 | Shimamoto et al. | 514/100 |
| 5,145,771 | 9/1992 | Lemasters et al. | 435/1 |
| 5,306,713 | 4/1994 | Suetsugu et al. | 514/100 |
| 5,480,773 | 1/1996 | Ogata et al. | 435/2 |

FOREIGN PATENT DOCUMENTS

| | | |
|---|---|---|
| 0127471 | 12/1984 | European Pat. Off. |
| 0324387 | 7/1989 | European Pat. Off. |
| 0339486 | 11/1989 | European Pat. Off. |
| 0590514 | 4/1994 | European Pat. Off. |
| 118817 | 11/1994 | European Pat. Off. |
| 2249937 | 5/1992 | United Kingdom |

OTHER PUBLICATIONS

Obata, Chemical Abstracts, vol. 118, No. 1 4 Jan. 1993, Columbus, Ohio U. S. Abstract No. 4606.

Tanemoto et al., Chemical Abstracts, vol. 119, No. 5, 2 Aug., 1993, Columbus, Ohio U.S. Abstract No. 40876.

Takayama et al., Chemical Abstracts, vol. 120, No. 7, 14 Feb. 1994, Columbus, Ohio U.S. Abstract No. 74626.

Tanemoto et al., Acta. Med. Okayama, 47(2) pp. 121–127 (1993).

*Primary Examiner*—Sandra E. Saucier
*Attorney, Agent, or Firm*—Wenderoth, Lind & Ponack

[57] ABSTRACT

This invention provides a hepatic graft preservative composition containing a phosphoric acid diester compound of the formula:

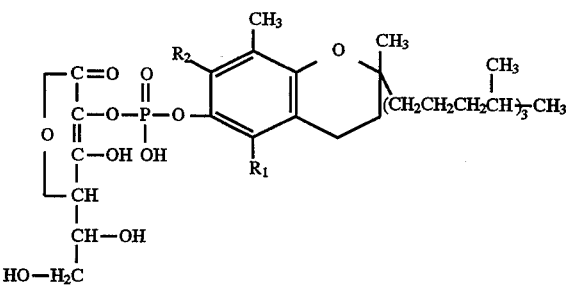

(wherein $R_1$ and $R_2$ are the same or different and each represents a hydrogen atom or a methyl group) or a pharmacologically acceptable salt thereof and a method for viable preservation of the hepatic graft using the above substance.

The hepatic graft preservative composition and hepatic graft preserving method of this invention inhibit hepatic microcirculation disturbance following cold storage-reperfusion of the liver to effectively prevent necrosis of hepatocytes and is, therefore, useful for the preservation of the hepatic graft.

7 Claims, 1 Drawing Sheet

METHOD FOR PRESERVING A LIVER BY PERFUSION WITH OR STORAGE IN A SOLUTION CONTAINING ASCORBYL TOCOPHERYL PHOSPHODIESTER

BACKGROUND OF THE INVENTION

1. Field of the Invention

This invention relates to an improved hepatic graft preservative composition and an improved method for viable preservation of the hepatic graft. More particularly, this invention relates to a viable liver preservative composition comprising an ascorbyl tocopheryl phosphate compound or a pharmacologically acceptable salt thereof and a method for viable preservation of the hepatic graft which comprises using said compound or salt.

2. Description of the Prior Art

For a successful organ transplantation, the organ resected from a donor must be kept functionally intact until it has been transplanted into a recipient. Each kind of organ has its own characteristics and, hence, requires a unique approach towards viable storage. However, the preservation principles applicable to all organs in common are to suppress metabolic consumption and preserve tissue ATP levels.

For the viable preservation of the liver for transplantation, there are two methods, namely the "simple cold storage method", which consists of initial perfusion with a preservative solution at 4° C. and subsequent immersion in a similar cold preservative solution and the "continuous hypothermic perfusion storage method", which involves the use of a machine. Clinically, however, the simple cold storage method using a preservative solution is generally employed. As the liver preservative, University of Wisconsin (UW) solution is generally employed. However, this solution has the disadvantage that the reduced glutathione contained as an active ingredient is very labile and easily oxidized in aqueous medium and, therefore, must be extemporaneously added, thus complicating the procedure. Moreover, UW solution is viscous and cannot be easily buffered so that it is not fully satisfactory for preservation of the hepatic graft. Moreover, with the conventional preservative solutions including said UW solution, hepatocytes tend to be damaged for some reasons or other so that deterioration of liver function cannot be successfully prevented.

Therefore, research and development efforts are being made in earnest for developing an improved hepatic graft preservative solution free from the above-mentioned disadvantages and insuring good graft preserving effects.

In the course of their ceaseless research into the pharmacology of ascorbyl tocopheryl phosphate compounds, the inventors of the current application discovered that these compounds have an inhibitory effect on microcirculation disorders of the liver and are useful for the viable preservation of the liver isolated for transplantation. This discovery was followed by further studies which have resulted in the development of this invention.

SUMMARY OF THE INVENTION

This invention provides a hepatic graft preservative composition containing a phosphoric acid diester compound and a new protocol for viable preservation of the hepatic graft which involves the use of said compound.

This invention is, therefore, directed to:

(1) A hepatic graft preservative composition comprising a phosphoric acid diester compound of the following formula or a pharmacologically acceptable salt thereof (hereinafter referred to briefly as the compound).

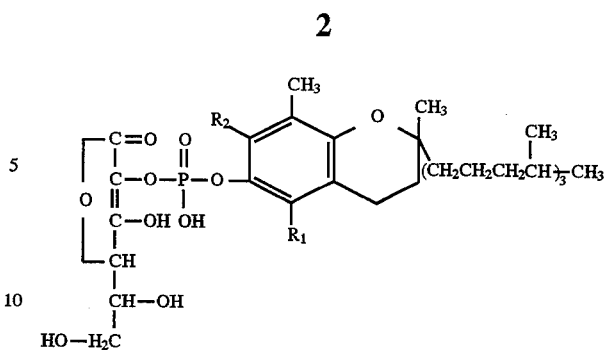

(wherein $R_1$ and $R_2$ are the same or different and each represents a hydrogen atom or a methyl group).

(2) The hepatic graft preservative composition as defined under (1) as provided in a liquid dosage form.

(3) The hepatic preservative composition as defined under (2) wherein said phosphoric diester compound or pharmacologically acceptable salt occurs in a concentration of $5 \times 10^{-9}$ g/ml to $1 \times 10^{-4}$ g/ml.

(4) The hepatic graft preservative composition as defined under (2) wherein said liquid dosage form has an osmolarity of 260 mOsm to 380 mOsm.

(5) The hepatic graft preservative composition as defined under (2) wherein said liquid dosage form has a pH value of 3 to 10.

(6) A method of preserving the hepatic graft which comprises using a liquid composition comprising a phosphoric acid diester compound or a pharmacologically acceptable salt as defined under (1) as ① an initial perfusate for intrahepatic perfusion at resection of the liver, ② a maintenance immersion or perfusion preservative and/or ③ a rinse for use prior to warm blood reperfusion.

DETAILED DESCRIPTION OF THE INVENTION

Figure 1:
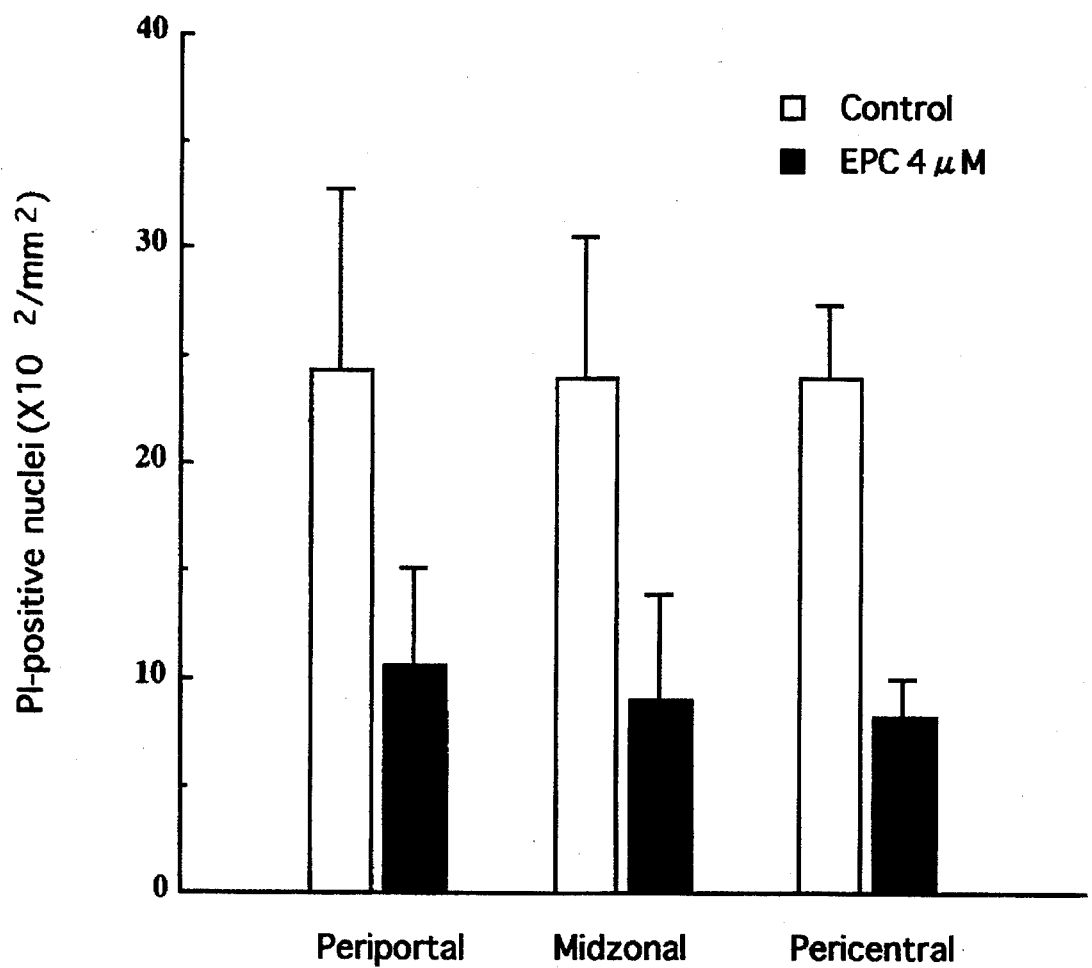
FIG. 1 is a diagrammatic representation of necrotized liver cell counts (propidium iodide (PI) fluorescene-positive nuclei; $(\times 10^2/mm^2)$ in the periportal zone (zone 1), midzonal zone (zone 2) and pericentral zone (zone 3) of the rat liver after cold storage-reperfusion in the control group and the compound-treatment group.

The term "hepatic graft preservative composition" is used in this specification to mean not only said initial perfusate but also said rinse unless contrary to the context in which the term appears.

The compound for use in the hepatic graft preservative composition and hepatic graft preserving method of this invention can be synthesized by inter alia the process in Japanese Patent Publication H-2-44478 or Japanese Patent Application Kokai S-62-205091, or any improvement thereof.

The compound for use in the hepatic graft preservative composition and hepatic graft preserving method of this invention is already known to be useful as an anticataract agent, a prophylactic and therapeutic agent for climacteric disturbance, a skin care cosmetic ingredient (Japanese Patent Publication H-2-44478), an antiinflammatory agent (Japanese Patent Publication H-1-27044), an antiulcer agent (Japanese Patent Application Kokai S-68-270626), a prophylactic and therapeutic agent for ischemic organic impairment (Japanese Patent Application Kokai H-2-111722) and a Maillard reaction inhibitor (Japanese Patent Application Kokai H-3-161444), among others.

The compound for use in the hepatic graft preservative composition and hepatic preserving method of this invention may be either of its free form or the form of a pharmacologically acceptable salt thereof. The pharmacologically acceptable salt that can be used includes salts with alkali metals such as sodium, potassium, etc. and salts with alkaline earth metals such as calcium and magnesium, among others. Other types of salts, if acceptable from pharmacologic points of view, can also be employed.

According to the clinical objective and need, more than one species of the compound can be incorporated, in an appropriate combination, in the hepatic graft preservative composition of this invention.

The compound for use as the active ingredient in the hepatic graft preservative composition and hepatic graft preserving method of this invention is a very safe substance with an extremely low toxic potential and, as such, can be used with advantage for the purposes of this invention. [e.g. the $LD_{50}$ values of L-ascorbyl DL-α-tocopheryl phosphate potassium (hereinafter referred to briefly as EPC-K)$\geq$5 g/kg p.o. (rats) and$\geq$100 mg/kg i.v. (rats)].

The liver preservative composition of this invention can be provided in a liquid form or supplied in a solid form for extemporaneous reconstitution. The solid form can be advantageously used as dissolved, suspended or emulsified in purified water, physiological saline or like medium. The solid form includes tablets, granules and powders, among others, which can be respectively manufactured by the known techniques. These preparations may contain conventional additives such as an excipient, binder, disintegrator, dispersant, reabsorption promoter, buffer, surfactant, solubilizer, preservative, emulsifier, isotonizing agent, stabilizer, pH control agent and so on.

Unless contrary to the object of this invention, the hepatic graft preservative composition of this invention may contain other organ-preserving ingredients which are generally used for the viable preservation of hepatic grafts. Among such ingredients are antibiotics, insulin, carbohydrates (glucose, mannitol, etc.), vitamins (vitamin C, vitamin E, etc.), organic acids (lactic acid, citric acid, etc.), nucleic acid bases (adenosine triphosphate etc.), antihypertensive agents (calcium-channel blockers, β-adrenergic antagonists, angiotensin-converting enzyme inhibitors, etc.), antiplatelet factor, antidiuretic hormone, anticoagulant (e.g. heparin) and so on.

Furthermore, the compound can be dissolved in any known organ preservative solution, such as Euro-Collins (EC) solution and University of Wisconsin solution [ViaSpan (registered trademark) produced by DuPont], to provide a hepatic graft preservative solution.

The proper concentration of the compound in the hepatic graft preservative composition of this invention is dependent on the species of compound, condition of the liver, and the necessary duration of preservation but the recommended final concentration in a liquid preparation is generally about $5\times10^{-9}$ g/ml to $1\times10^{-4}$ g/ml and preferably about $1\times10^{-7}$ g/ml to $1\times10^{-6}$ g/ml.

The osmolarity of such a liquid hepatic graft preservative composition of this invention is adjusted, by known means, to about 260 mOsm to about 360 mOsm, preferably about 275mOsm to about 320 mOsm. The pH of the liquid preparation should also be adjusted, by known means, to about 3 to 10, preferably about 4 to 9.

The temperature suited for the hepatic graft preservation employing the preservative composition of this invention is dependent on the species and concentration of compound, condition of the liver and the desired duration of preservation but is generally about −5° C. to 20° C., preferably about 0° C. to about 15° C. and, for still better results, about 4° C.

In preserving the isolated liver with the hepatic graft preservative composition of this invention, the known organ cassette, module and other hardware can be utilized.

The hepatic graft preservative composition of this invention can be employed ① as initial perfusate for intrahepatic perfusion at resection of the liver, ② as a maintenance immersion or perfusion storage solution, and/or ③ as a rinse preceding warm blood reperfusion. Thus, using the liquid hepatic graft preservative composition of this invention within the temperature range mentioned above, the fresh liver is subjected initial perfusion from the portal vein for about 1 to 10 minutes to wash out the blood from the tissue. Then, this initially perfused graft is maintained in, or under perfusion with, a suitable amount of the liquid preservative composition of this invention within the temperature range mentioned hereinbefore. Finally, prior to reperfusion with the warm blood after transplantation, the liver is rinsed with the liquid hepatic graft preservative composition of this invention.

EXAMPLES

The following example and formulation examples are intended to illustrate this-invention in further detail and should by no means be construed as defining the scope of the invention.

Example 1

Hepatocyte-protecting effect of the compound in the rat liver cold storage-reperfusion injury model The hepatocyte-protecting effect of the compound in the rat liver cold storage-reperfusion injury model was studied using a rat perfused liver microcirculation monitoring system developed by the inventors of this invention.

[Test substance]L-Ascorbyl DL-α-tocopheryl phosphate potassium (abbreviation: EPC-K).

[Method]Livers from male Wistar rats with body weights 300 g to 330 g were perfused with Solution I[1)] to wash out the blood thoroughly and stored in a control group (Solution II[2)]) and an EPC-K group (Solution II containing $4\times10^{-6}$M EPC-K) at 4° C. for 90 minutes. After this cold storage, Solution I containing 1 μM propidium iodide (PI) was injected at a flow rate of 3.0 ml/min/g liver weight in one direction from the portal vein and after one hour of this perfusion the injury to the cells (severity of cell necrosis) in the hepatic microcirculation was assessed in terms of PI-positive nuclei, i.e. injured nuclei forming a fluorescent complex, by the technique of liver microcirculation viviperception. The stained nuclear image was input as a video picture using a high-sensitivity imaging apparatus (Silicon Intensified Target Camera, Hamamatsu Photonics) through an inverted type biomicroscope and the number of PI-positive nuclei per unit area was analyzed in the three strata of (1) periportal zone (zone 1), (2) midzonal zone (zone 2), and (3) pericentral zone (zone 3) according to the method described in the literature (Lab. Invest. 67, 434–442, 1992). Thus, one hour after initiation of reperfusion, fluorescein isothiocyanate-labelled albumin (2%, 100 μl, bolus) was infused into the portal vein and the locations of the terminal branch of the portal vein (PV) and the central vein (CV) were determined. The area within a circle drawn with a radius of 70 μm about PV and that about CV were defined as zone 1 and zone 3, respectively, while the remaining intermediate zone was defined as zone 2. A circle of the same radius was marked off at random within zone 2 and the number of PI-positive nuclei within the circle was counted as data for zone 2.

| 1) 95% $O_2$/5% $CO_2$-saturated Krebs-Henseleit solution | |
| --- | --- |
| Sodium chloride | 118.5 mM |
| Potassium chloride | 4.7 mM |
| Calcium chloride | 2.5 mM |
| Potassium dihydrogen phosphate | 1.2 mM |
| Magnesium sulfate | 1.2 mM |
| Sodium hydrogen carbonate | 20.0 mM |
| 2) Euro-Collins solution | |
| Potassium monohydrogen phosphate | 740 mg |
| Potassium dihydrogen phosphate | 205 mg |
| Potassium chloride | 112 mg |
| Sodium hydrogen carbonate | 84 mg |
| Glucose | 3.5 g |
| Water for injection | q.s. |
| Total | 100 ml |

[Results] The results are shown in FIG. 1.

It is apparent from FIG. 1 that the composition of this invention inhibits the liver microcirculation disturbance after rat liver cold storage-reperfusion to effectively prevent necrosis of liver cells, suggesting that the composition is of value as a hepatic Kraft preservative.

Example 2

| EPC-K | 0.3 mg |
| --- | --- |
| Potassium chloride | 0.12 g |
| Calcium chloride | 15 mg |
| Magnesium chloride | 5 mg |
| Sodium chloride | 0.8 g |
| 1N-Hydrochloric acid | q.s. |
| 1N-Sodium hydroxide | q.s. |
| Water for injection | q.s. |
| Total | 100 ml |
| | pH 7.3 |

The above ingredients are mixed in the conventional manner to provide a hepatic graft preservative solution.

Example 3

| EPC-K | 0.1 mg |
| --- | --- |
| Potassium dihydrogen phosphate | 0.25 g |
| Sodium citrate | 0.1 g |
| Potassium chloride | 0.85 g |
| Magnesium chloride | 15 mg |
| Calcium chloride | 15 mg |
| Sodium chloride | 0.1 g |
| 1N-Hydrochloric acid | q.s. |
| 1N-Sodium hydroxide | q.s. |
| Water for injection | q.s. |
| Total | 100 ml |
| | pH 7.3 |

The above ingredients are mixed in the conventional manner to provide a liver graft preservative solution.

Example 4

| EPC-K | 0.1 g |
| --- | --- |
| Mannitol | 5 g |
| Water for injection | q.s. |
| Sodium hydroxide | q.s. |
| Total | 100 ml |
| | pH 7.3 |

The above ingredients are mixed in the conventional manner and filled in 2 ml-glass ampules to provide an injectable solution.

This solution is extemporaneously mixed with an appropriate amount of an organ preservative solution, such as Euro-Collins or ViaSpan solution, to provide a hepatic graft preservative solution.

Example 5

| EPC-K | 10 mg |
| --- | --- |
| Sucrose | 500 mg |

The above solid composition is filled in 5 ml-glass vials in the conventional manner to provide a hepatic graft preservative.

This preservative is extemporaneously dissolved in a suitable amount of an organ preservative solution, such as Euro-Collins or ViaSpan solution, to provide a hepatic graft preservative solution.

Example 6

Using about 500 to 2000 ml of the hepatic graft preservative solution (4° C.) prepared in Example 3, the fresh cadaver liver was subjected to initial perfusion for about 2 minutes and then stored in the same preservative solution at 4° C.

The hepatic graft preservative composition and hepatic graft preserving method of this invention inhibit hepatic microcirculation disturbance following cold storage-reperfusion of the liver to effectively prevent necrosis of hepatocytes and is, therefore, useful for the preservation of the hepatic graft.

What is claimed is:

1. A method of preserving a liver prior to transplantation comprising: treating the liver with a liquid composition comprising the compound of the formula

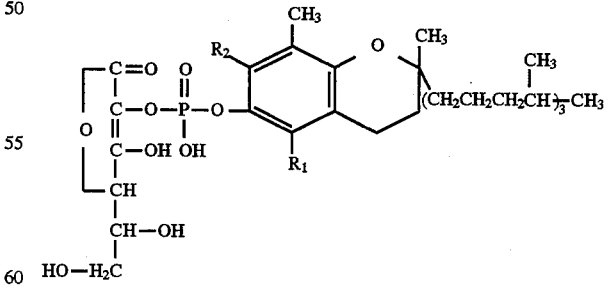

wherein $R_1$ or $R_2$ are the same or different and each is a hydrogen atom or a methyl group, or a pharmacologically acceptable salt thereof in a concentration of $5 \times 10^{-9}$ g/ml to $1 \times 10^{-4}$ g/ml.

2. The method of claim 1 wherein the liquid composition has an osmolarity of 260 mOsm to 360 mOsm.

3. The method of claim 1 wherein the liquid composition has a pH value of 3 to 10.

4. The method of claim 1 wherein the treating is conducted at a temperature of −5° to 20° C.

5. The method of claim 1 wherein the treatment is perfusing the liver with the liquid composition.

6. The method of claim 1 wherein the treatment is immersing the liver in the liquid composition.

7. The method of claim 1 wherein the treatment is perfusing the liver with the liquid composition and immersing the liver in the liquid composition.

* * * * *